United States Patent [19]
Klein et al.

[11] Patent Number: 5,413,686
[45] Date of Patent: May 9, 1995

[54] MULTI-CHANNEL AUTOMATED CAPILLARY ELECTROPHORESIS ANALYZER

[75] Inventors: Gerald L. Klein, Orange; Gary A. Miller, Yorba Linda, both of Calif.

[73] Assignee: Beckman Instruments, Inc., Fullerton, Calif.

[21] Appl. No.: 916,308

[22] Filed: Jul. 17, 1992

[51] Int. Cl.⁶ .................. G01N 27/26; G01N 27/447
[52] U.S. Cl. ......................... 204/299 R; 204/180.1
[58] Field of Search ............ 204/299 R, 180.1, 182.8

[56] References Cited

U.S. PATENT DOCUMENTS

| | | | |
|---|---|---|---|
| 3,932,264 | 1/1976 | Haruki et al. | 204/299 R |
| 3,956,099 | 5/1976 | Israel et al. | 204/299 R |
| 4,124,470 | 11/1978 | Dahms | 204/180.1 |
| 4,154,669 | 5/1979 | Goetz | 204/299 R |
| 4,284,491 | 8/1981 | Vesterberg | 204/299 R |
| 4,298,570 | 11/1981 | Liggig et al. | 422/64 |
| 4,375,401 | 3/1983 | Catsimpoolas | 204/301 |
| 4,394,263 | 7/1983 | Dosch et al. | 210/198.2 |
| 4,747,919 | 5/1988 | Anderson | 204/299 R X |
| 4,816,123 | 3/1989 | Ogan et al. | 204/183.3 |
| 4,865,090 | 9/1989 | Burolla et al. | 141/165 |
| 4,906,344 | 3/1990 | Hjerten | 204/182.8 |
| 4,911,807 | 3/1990 | Burd | 204/180.1 |
| 4,927,265 | 5/1990 | Brownlee | 356/73 |
| 4,985,129 | 1/1991 | Burd | 204/299 R |
| 5,019,236 | 5/1991 | Young | 204/299 R |
| 5,045,172 | 9/1991 | Guzman | 204/299 R |
| 5,066,382 | 11/1991 | Weinberger et al. | 204/299 R |
| 5,085,757 | 2/1992 | Karger et al. | 204/299 R |
| 5,169,511 | 12/1992 | Allington et al. | 204/180.1 X |
| 5,173,163 | 12/1992 | Tehrani | 204/299 R |

FOREIGN PATENT DOCUMENTS 0339779 11/1989 European Pat. Off. .

OTHER PUBLICATIONS

"Evaluation of an Automatic Siphonic Sampler for Capillary Zone Electrophoresis", by Honda, Iwase and Fujiwara, *Journal of Chromatography*, vol. 404 (1987) pp. 313–320.

"Capillary Zone Electrophoresis", by Jorgenson and Lukacs, *Science*, vol. 222, pp. 266–272.

"Characterization and Automation of Sample Introduction Methods for Capillary Zone Electrophoresis," by Rose and Jorgenson, *Anal. Chem.* 1988, vol. 60, No. 7, pp. 642–648.

"Quantitation of Picogram Quantities of Serum Albumin by Ultramicrodisc Electrophoresis and Direct Densitometry," by Oken, *Microchemical Journal*, vol. 15, (1970), pp. 557–563.

*Primary Examiner*—John Niebling
*Assistant Examiner*—John S. Starsiak, Jr.
*Attorney, Agent, or Firm*—William H. May; Arnold Grant; Gary T. Hampson

[57] ABSTRACT

An automated multi-channel capillary electrophoresis analyzer includes a plurality of capillaries having first and second ends. The first ends of the capillaries are adapted to be collectively transported to and from selected reagent reservoirs. The second ends of the capillaries are removably and sealable retained within a common manifold that is in turn in selectable fluid communication with selected reagents and a vacuum source.

56 Claims, 7 Drawing Sheets

MULTI-CHANNEL AUTOMATED CAPILLARY ELECTROPHORESIS ANALYZER

FIELD

The present invention relates generally to the field of electrophoresis and more particularly to capillary electrophoresis, and still more particularly to an automated capillary electrophoresis analyzer that may be used for the batch or parallel analysis of a plurality of samples. The invention may be used in, but is not limited to, clinical chemistry.

BACKGROUND

The value of electrophoresis in clinical chemistry has been recognized for some time in the analysis, for example, of proteins in serum as well as other body fluids. Typically, gel electrophoresis is the method of choice in clinical chemistry laboratories. With gel electrophoresis, a sample is applied near one edge of a layer of gelatin carried on a flexible sheet, usually called a "gel". The gel is electrophoresised, stained and the density of the resulting pattern is measured to reveal the proteins contained in the sample. Although gel electrophoresis is relatively inexpensive in terms of the supplies and equipment required to perform sample analyses, the technique requires skilled technicians and is time consuming, effectively resulting in a high price per test and limiting the number of tests that can be performed using the technique.

Efforts have been made to automate electrophoresis in the clinical laboratory. For example, U.S. Pat. No. 4,124,470 to Dahms describes a zone electrophoresis apparatus where a number of samples in individual large-bore tubes can be processed serially on a turntable. Although this apparatus automates the electrophoresis process, it requires large volumes of electrophoresis reagents, such as buffer and the like, and the use of wicks and membranes as part of the electrophoresis circuit.

Capillary electrophoresis is a more recent development and can be used to perform the type of electrophoretic separations presently performed with gels. In capillary electrophoresis, a small tube or capillary having an inside bore diameter in the range of about five microns to about two hundred microns and often about twenty cm long is filled with an electrically conductive fluid, or buffer. A small quantity of a sample to be analyzed is introduced into one end of the capillary bore and the ends of the capillary are placed into separate reservoirs of buffer. A direct current voltage in a range of about 2,000 volts to about 30,000 volts is applied to the ends of the capillary by means of electrodes positioned in the buffer reservoirs, causing a small current, typically in the range of about five microamps to about one milliamp, to flow through the capillary.

With the correct polarity applied across the capillary, the sample begins to migrate from the sample introduction end toward the other end of the capillary. As this migration occurs, different molecules in the sample travel at different rates primarily because of slightly different electrical charges on the molecules. These different migration rates cause molecules with slightly different charges to separate one from the other, some moving more quickly and advancing relatively with respect to more slowly moving molecules. As the sample nears the other end of the capillary, the small volume of sample becomes separated into bands of different molecules according to the relative migration rates of the molecules. These bands or groups of different molecules are detected near the other end of the capillary by, for example, passing a light beam through the bore of the capillary. Changes to the light beam, such as absorbance caused by the different molecules, are detected as the separated molecules pass through the beam, thus identifying the different molecules or the classes or categories of molecules in the sample and the relative concentration of such molecules.

Automated forms of capillary electrophoresis analyzers are known in the art. For example European Patent Application number 89302489.3, publication number 0,339,779 A2, corresponding to U.S. patent application Ser. No. 188,773, filed Apr. 29, 1988 (Burolla) describes an automated capillary electrophoresis apparatus. That apparatus includes two conveyors for positioning vials under ends of a capillary mounted in a cartridge. The ends of the capillaries along with electrodes are inserted into the vials by means of hypodermics that pierce caps on the vials. A single detector provides detection of electrophoresised samples.

Another automated capillary electrophoresis apparatus is described in U.S. Pat. No. 5,045,172 to Guzman. The Guzman apparatus includes two rotating tables at opposite ends of the apparatus that hold sample and buffer cups. A capillary, which is described in Guzman as being a single capillary or a plurality of capillary tubes operated in parallel or in a bundle, has two opposite ends. These ends are positioned by automated arms and posts in respective corresponding pairs of cups to first draw sample into the capillary and to then electrophorese the sample. As with Burolla, a single detector is used to detect the results.

Neither of the automated analyzers just described, however, is suitable for routine clinical laboratory applications. Each of such analyzers requires considerable manual manipulation despite their automated nature, such as preparing and placing individual sample and buffer vials onto the analyzer, programming the analyzer for the various analytical routines, and the like. Because only one sample can be electrophoresed and detected during each analysis cycle of the analyzers, the number of samples per unit time, or throughput, is severely restricted as compared to the needs of most routine clinical laboratory work.

Yet another disadvantage of the Guzman analyzer is that it appears difficult to replace the capillary. While the capillary in Burolla is easy to replace because it is contained within a cartridge, the Burolla cartridge adds expense to the use of the analyzer. Further, the commercial version of the Burolla analyzer (available from Beckman Instruments, Inc., Fullerton, Calif. U.S.A. under the trademark P/ACE) requires an external high-pressure nitrogen tank, adding to the expense and inconvenience of use of the analyzer in a clinical chemistry environment.

Thus, there is a need for an automated capillary electrophoresis analyzer that is easy to use, requires less sample manipulation, is relatively inexpensive, and is capable of substantially increased throughput as compared to prior capillary electrophoresis analyzers. There is also a need for an automated capillary electrophoresis analyzer that can be easily adapted for use in a clinical chemistry laboratory.

SUMMARY OF THE INVENTION

The present invention is directed to a capillary electrophoresis analyzer that can simultaneously analyze a plurality of samples. In one embodiment, an apparatus in accordance with the present invention includes a plurality of capillaries, each having a first end and and second end. A conduit or manifold includes means for receiving the second ends of the capillaries. The conduit may include means for removeably sealing the second ends of the capillaries within the conduit there thereby establish a common liquid path between the second ends of the capillaries.

The apparatus in accordance with the present invention may be adapted for use with samples retained within reagent segments wherein the reagent segments have a plurality of wells. Such an apparatus accordingly includes a plurality of capillaries, each capillary having a first open end and a second open end. There is provided means for simultaneously positioning a first end of each of the capillaries into selected distinct ones of the reagent segment wells. The apparatus also includes a manifold defining a common conduit including means for receiving the second end of each of the capillaries into the common conduit to establish a common liquid path between the second ends of the capillaries. An electrode is provided in the manifold for establishing one end of the direct current circuit through the capillaries.

The apparatus may also be provided with individual detection means for each of the capillaries. The individual detection means may provide for optical detection of each of the capillaries individually and simultaneously, and can thus detect the results of electrophoresising occurring essentially simultaneously in each of the capillaries.

The apparatus may also include a turntable for receiving a plurality of samples and a pipettor-dilutor for transferring samples to the wells of the reagent segment and diluting the sample as such transfer is made and performing subsequent dilutions as may be required for the particular sample involved. Advantageously, the samples may be contained in standard blood tubes that are supported by the turntable for direct use by the apparatus without transfer to other containers, thus avoiding contamination and possible inadvertent spread of infectious materials.

To position the capillaries within the appropriate wells of the reagent segments, the turntable carrying the reagent segments can be elevated toward and away from the first ends of the capillaries. Alternatively, the capillaries may be mounted on a suitable elevator platform that can be lowered and raised to either place the capillary first ends into or remove such ends from the respective wells of the reagent segments.

The apparatus may also include running buffer and wash solution dispensing means for dispensing running buffer and wash solution into appropriate wells of the reagent segments. Further, running buffer and vacuum source means may be in fluid communication via suitable valving means with the manifold. With vacuum applied to the manifold, liquid is drawn simultaneously through the capillaries to the manifold. The liquid may be wash solution, running buffer, or small quantities or slugs of sample. Running buffer may then be valved into the manifold and running voltage applied to the capillaries to simultaneously electrophorese and detect a plurality of samples.

To essentially simultaneously detect the results of the electrophoresis, the apparatus may include optical detection means for each of the capillaries. In the embodiment disclosed herein, the optical detection means includes an input and out optical fiber and optical detector for each capillary. A single light source is used to provide illumination to all of the input optical fibers, further simplifying the apparatus of the present invention.

Thus, the apparatus of the present invention overcomes of the limitations and disadvantages of the prior art, and provides an easy-to-use and maintain capillary electrophoresis apparatus which enables the simultaneous electrophoresis and detection of a plurality of samples. The apparatus includes sample handling onboard and may be easily adapted for routine clinical laboratory use.

BRIEF DESCRIPTION OF THE DRAWINGS

These and other features, aspects, and advantages of the present invention will become better understood with reference to the following description, appended claims, and accompanying drawings where:

DETAILED DESCRIPTION

Figure 1:
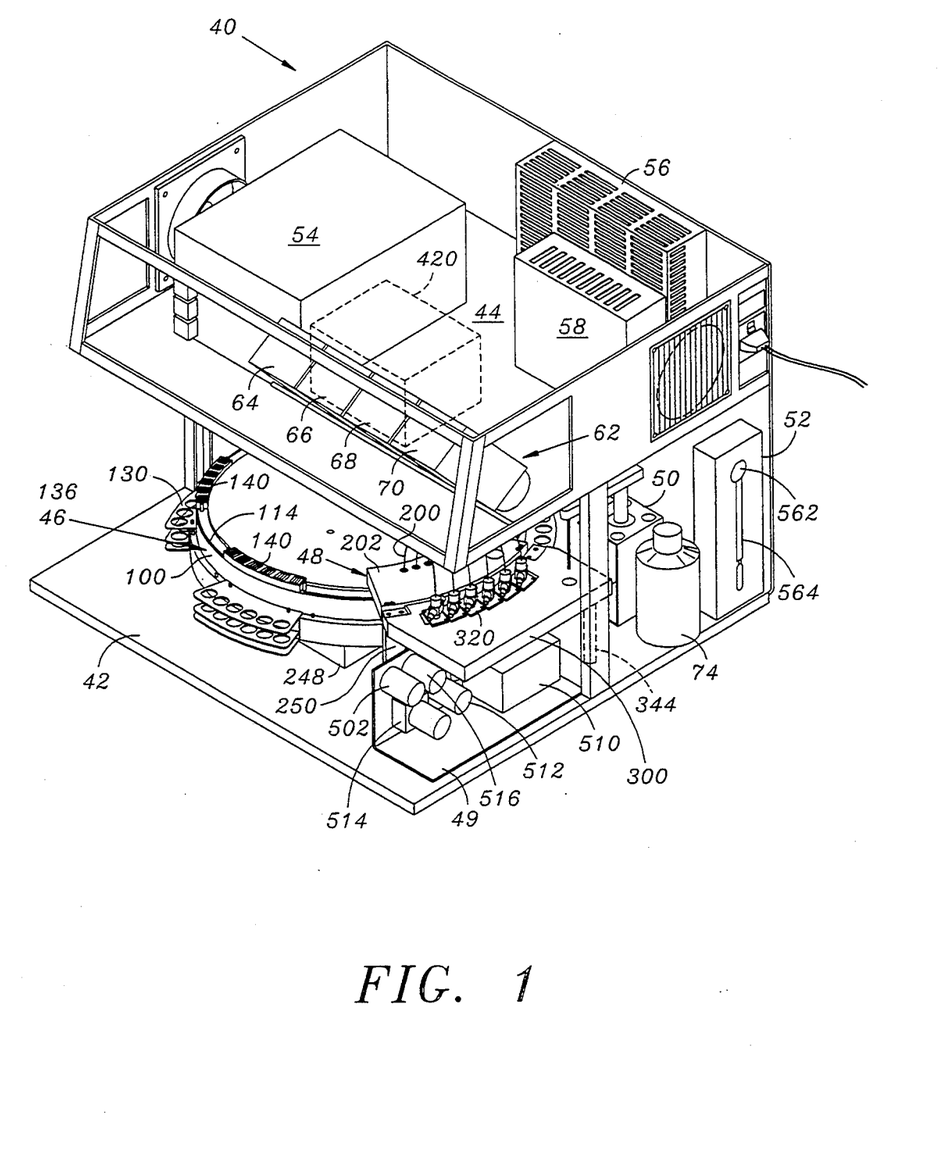
FIG. 1 is a perspective view of an analyzer in accordance with the present invention.
Figure 2:
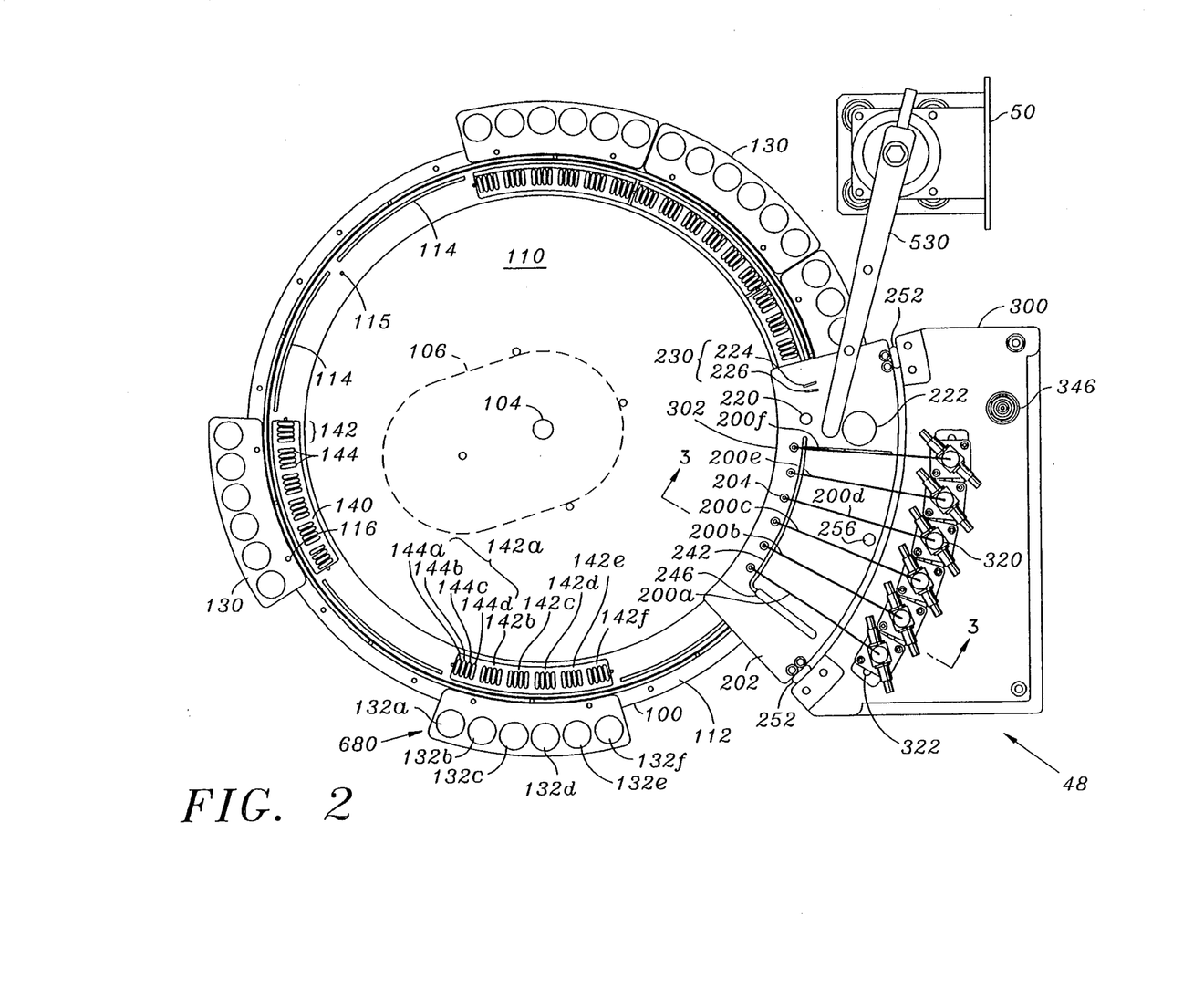
FIG. 2 is a top view of the turntable, capillary sample end platform and capillary detection end platform of the analyzer of FIG. 1.

With respect to FIGS. 1 and 2, an analyzer 40 in accordance with the present invention is formed on a chassis having a lower horizontal mounting plate 42 and an upper horizontal mounting tray 44. The mounting plate 42 supports a turntable assembly 46, a capillary assembly 48, a fluid control assembly 49, a probe assembly 50, and a pipettor-dilutor assembly 52. The upper mounting tray 44 supports a card cage 54, low voltage DC power supply 56, and light source power supply 58. A plurality of reagent reservoirs 62 are also supported at the front edge of the upper tray for easy access by an operator. Preferably, the reservoirs 62 include a water bottle 64, a buffer bottle 66 containing a suitable running buffer such as boric acid at pH 10.2, a wash solution bottle 68 containing sodium hydroxide (NaOH), and a diluent bottle 70 containing a suitable diluent such as phosphate buffered saline. The diluent may additionally include if desired specific chemical reference markers, such as is disclosed in U.S. patent application Ser. No. 708,424, filed May 31, 1991 in the name of Fu-Tai A. Chen, and entitled Identification of Sample Constituents Utilizing Capillary Electrophoresis. The placement of the reservoirs 62 on the upper tray 44 allows gravity feed of the reagents contained in the reservoirs 62 throughout the analyzer 40. The analyzer 40 may also include suitable top, side and front panels and doors (not shown in FIG. 1) to enclose the analyzer 40, all in a conventional fashion.

The turntable assembly 46 provides support and automated positioning for sample tubes and reagent segments. More particularly, the turntable assembly 46 includes a turntable 100 rotatably supported by a shaft 104 at the center of the turntable 100. The shaft 104 is part of a motor and drive belt assembly 106 (shown in simplified phantom outline in FIG. 2) that is supported by the mounting plate 42 and is beneath and inside the turntable 100. The motor and drive belt assembly 106 is operated so as to rotate the turntable 100 and shaft 104 in a controllable fashion.

The turntable 100 includes an upper surface 110 and a lower annular support 112. The upper surface 110 includes a plurality of arcuate ribs 114 disposed near the outer periphery of the upper surface 110 and, in the embodiment disclosed herein, the ribs 114 define ten equally spaced positions about the periphery of the upper surface 110. Between the ribs 114 are pins 115. The lower annular support 112 includes posts 116 extending upwardly from the surface 112. Pairs of posts 116 are disposed radially outwardly with respect to each of the ribs 114. Thus, twenty posts 116 are disposed on the annular support 112 with respect to the ten corresponding ribs 114.

The turntable 100 also includes an inner depending lip 118 (FIG. 3) that includes ten equally spaced notches (not shown) formed into the lower edge of the lip 118. The notches are sized to be detected by an optical detector (not shown) to thus determine the rotational position of the table 100, all in a conventional fashion.

Sample tube sectors 130 may be suspended from the annular support 112 and posts 116 to support a plurality of sample tubes, such as blood draw or sample tubes 132, about the periphery of the turntable 100. The sample tube sectors 130 include a horizontal flange 134 that is adapted to rest upon the annular support 112 and two holes 136 that receive the posts 116 to thereby removably secure the sample sector 130 to the turntable 100, the horizontal flange 134 resting upon the annular support 112.

A plurality of reagent segments 140 may be removably positioned about the periphery of the upper surface 110. Each reagent segment 140 is curved to match the curve at the periphery of the upper surface 110. The reagent segments fit over the ribs 114, the ribs 114 thus fitting inside the reagent segments 140 near the outer edges thereof, thereby removeably retaining the reagent segments 140 on the upper surface 110. The reagent segment 140 includes six reservoir groups 142 and each reservoir group 142 in turn includes four individual reservoirs 144. Each reservoir 144 is adapted to hold approximately 200 μl of liquid when filled to the maximum usable capacity. Five reagent segments 140 are seen in FIG. 2.

The capillary assembly 48 provides support for a plurality of capillaries as well as the associated electrodes for establishing current flow through the capillaries and optical fiber holders for positioning optical fibers used for detection. As used herein, the "sample end" of a capillary is the end into which a sample is introduced into the capillary before electrophoretic separation along the length of the capillary, and the "detection end" of a capillary is the end proximate the detection or detector means used to detect the results of electrophoretic separation occurring along the length of the capillary.

In the embodiment disclosed herein, the capillary assembly 48 supports six capillaries 200, also sometimes identified individually in this specification and in the Figures as capillaries 200a–200f as appropriate. The capillaries 200 are conventional silica quartz glass capillaries formed with a thin conformal coating of a polyimide, having an inside diameter within a range of about five microns to two hundred microns and more particularly in a range of approximately twenty five microns to seventy five microns, and an outer diameter of about one hundred forty microns to three hundred seventy five microns, respectively.

Figure 4:
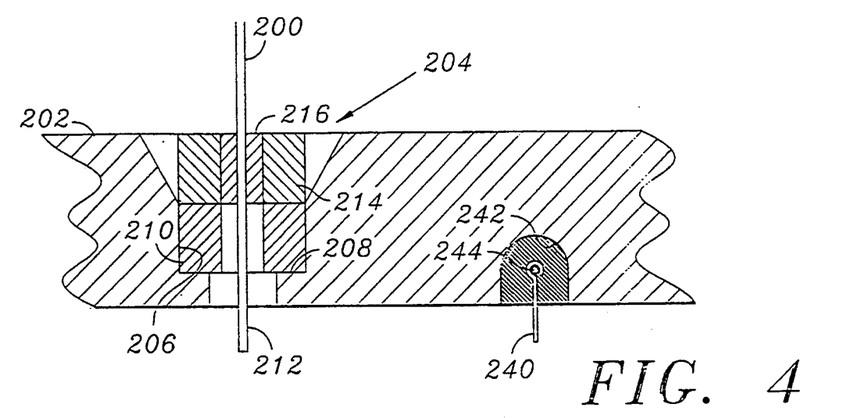
FIG. 4 is an enlarged side section view of the sample end of the capillaries.

The sample ends of the capillaries 200 are removably supported by a sample end plate 202. The sample end plate 202 is generally arcuate and includes six capillary end retainers 204 (FIG. 4). The vertical center lines of the capillary end retainers 204 are spaced to align with the spacing between corresponding ones of the reservoirs 144 within the reservoir groups 142 of a reagent segment 140 positioned on the turntable 100. This spacing aligns the ends of the capillaries 200 over, for example, a first one of the reservoirs 144 within each reservoir group 142 when so positioned by the rotation of the turntable, and so on.

Each of the retainers 204 includes a shouldered hole 206 through the sample end plate 202 defining an annular shoulder 208. A polarized barium ferrite annular magnetic 210 is fixed within the hole 206 against the shoulder 208.

To be retained by the sample end plate 202, sample end 212 of each of the capillaries 200 includes a second polarized barium ferrite annular magnet 214 bonded to the capillary 200 proximate the sample end 202 by means of a suitable rubber adhesive 216. With the capillary 200 positioned as illustrated in FIG. 4, the abutting ends of the magnets 210 and 214 are reverse polarized respectively, creating an attractive magnetic force between the magnets 214 and 210. The magnetic force thereby removably retains the capillary 200 within the sample end plate 202 and positions the sample end 212 for access to reservoirs 144 within a reagent segment 140 that may be carried by the turntable 100.

Two access holes 220 and 222 are formed through the sample end plate 202, the access hole 222 having a larger diameter than the access hole 220. The access hole 220 is formed to align over reservoirs 144 in reagent segments 140 that may be positioned on the turntable 100 beneath the sample end plate 202. The access hole 222 is aligned to provide access through the sample end plate 202 to sample tubes 132 that are held by the sample tube sectors 130 beneath the sample end plate 202.

Figure 5:
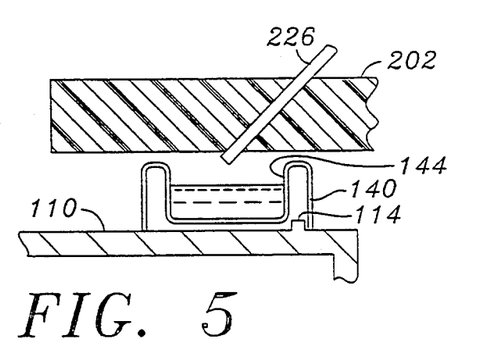
FIG. 5 is a side section view of a reagent delivery tube positioned to delivery reagent to a reagent segment.

Two lengths of small bore rigid tubing 224 and 226 are retained by the sample end plate 202 proximate the smaller access hole 220. Tubing lengths 224 and 226, forming a group 230 of reagent dispensing tubes, are of sufficient length to pass through the sample end plate 202 (FIG. 5) and are fixed at a slight angle with respect to vertical. The group 230 of tubes is positioned to deliver liquid reagents to reservoirs 144 of reagent segments 140 that may be positioned beneath the open ends of the tubing lengths 224 and 226 under the sample end plate 202.

The sample end plate 202 includes a plurality of bare wire electrodes 240 (FIGS. 3 and 4) depending from the lower surface of the sample end plate 202 and radially aligned with respect to the center of the turntable 100 with corresponding ones of the capillary end retainers 204. Thus in the embodiment disclosed herein, there are six such electrodes 240 corresponding to the six capillary end retainers 204. The electrodes 240 are fixed by means of a rubber adhesive within a groove 242 formed on the lower side of the sample end plate 202 and are connected to a wire 244 disposed within the groove 242. The wire 244 is routed through a larger intersecting groove 246 and is likewise retained within the larger groove 246 by a suitable rubber adhesive. The wire 244 and thus the electrodes 240 are connected to one output terminal of a high voltage d.c. power supply 248 via a suitable insulated wire (not shown).

The sample end plate 202 is adapted for vertical displacement with respect to the horizontal turntable 100. Posts 250 (one of which is shown in FIG. 1) are fixed to the mounting plate 42 and in turn support linear bearings 252 that are fixed to the outer corners of the plate 202. An elevator stepper motor 254 vertically actuates a shaft 256 that is in turn fixed to the plate 202. Actuation of the stepper motor 254 accordingly raises and lowers the plate 202 between mechanical stops defining the plate 202 up and down positions.

The capillary assembly 48 also includes a manifold plate 300. The manifold plate 300 is mounted atop the posts 250 and a support post 344 and includes an arcuate edge proximate the outer edge of the sample end plate 202. The manifold plate 300 supports six detection stations 320 that are aligned above a conduit or manifold 322 formed in the interior of the manifold plate 300. In the embodiment disclosed herein, the manifold 322 is in the form of an arcuate groove 323 formed into the manifold plate 300 above a larger arcuate groove 324. A bare wire electrode 325 is disposed within the arcuate groove 323 throughout the length of the arcuate groove 323. The electrode 325 exits through and is sealed within a hole (not shown) formed through the manifold plate 300 and is connected to system ground. An arcuate closing piece 326 is sealed within the larger arcuate groove 324 to close the manifold 322.

To provide access to the manifold 322 by the capillaries 200, six holes 328 (FIGS. 3 and 7) are formed through the upper surface of the manifold plate 300, the holes 328 each including a shoulder 330 reducing to a smaller diameter portion 332 of the hole 328. An annular seal 334 is fixed within the hole 328 and includes an internal taper 336 for directing the end of the capillary 200 into the manifold 322 as is described hereinbelow.

Two tubing couplings 338 and 340 (FIG. 6) are fixed within holes formed through the closing piece 326 and are in communication with the manifold 322, the tubing couplings 338 and 340 thus providing a liquid communication path with the manifold 322.

Figure 6:
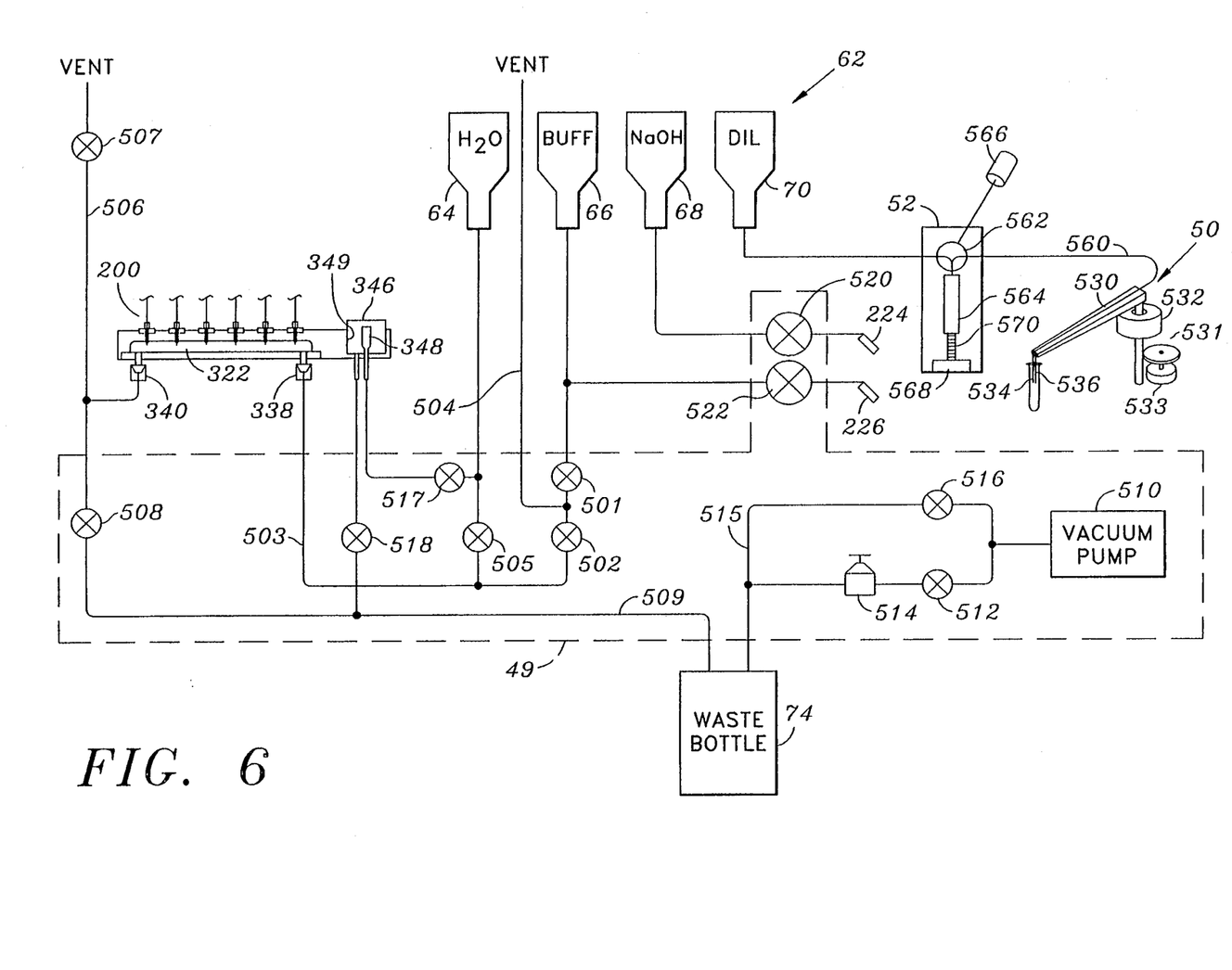
FIG. 6 is a simplified functional diagram of the fluid system of the analyzer of FIG. 1.

The manifold plate 300 also includes a wash station 346 (FIGS. 2 and 6). The wash station 346 includes an inner open-top fountain 348. Water solution may be feed through a port in the bottom of the fountain 348, overflowing the top of the fountain 348 into a catch basin 349. The catch basin 349 in turn includes a drain port through which wash effluent may be removed from the wash station 346.

The six detection stations 320 are coaxially aligned above the corresponding six holes 328 and seals 334. Each of the detection stations 320 includes vertical support structures 350 and 352 (FIG. 7) having transverse extending arms 354 and 356 with threads 358 and 360 formed on the outside of the arms 354 and 356. The vertical support structures 350 and 352 are adapted to receive the detection ends of the capillaries 200 and input and output optical fiber assemblies.

Figure 7:
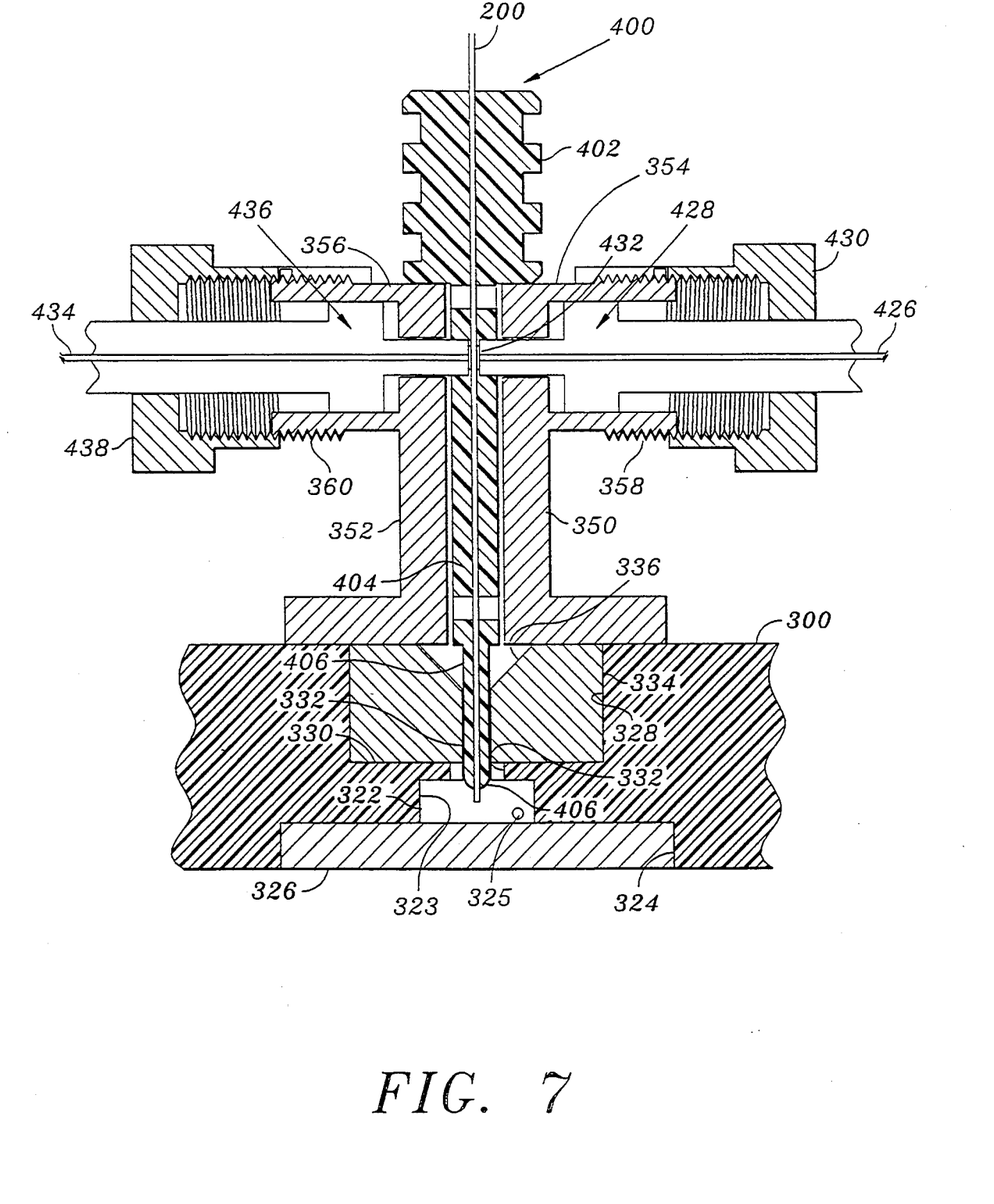
FIG. 7 is a cross-section view of a detection station for the detection end of capillaries.

The detection end of each the capillaries 200 is retained within a holder 400 that is formed around the capillary 200. The holder 400 includes a handle portion 402, a flattened portion 404 and a cylindrical downstream portion 406 that forms a fluid seal around the capillary 200. The downstream portion is adapted to be received by the seal 334 to establish a sealing relationship between the downstream portion 406 and the seal 334.

In the analyzer 40 of the present invention, light for the detection of the sample constituents within the capillaries 200 is brought to the capillaries 200 by fiber optics and is lead from the capillaries 200 to suitable detectors by means of fiber optics. More particularly, a single deuterium lamp within a heat sink housing 420 (mounted beneath the mounting tray 44 as shown in phantom in FIG. 1) is directed to a single optical fiber light guide 422 (FIG. 3) which is in turn split at an optical fiber splitter 424 into six input optical fiber light guides 426.

Figure 3:
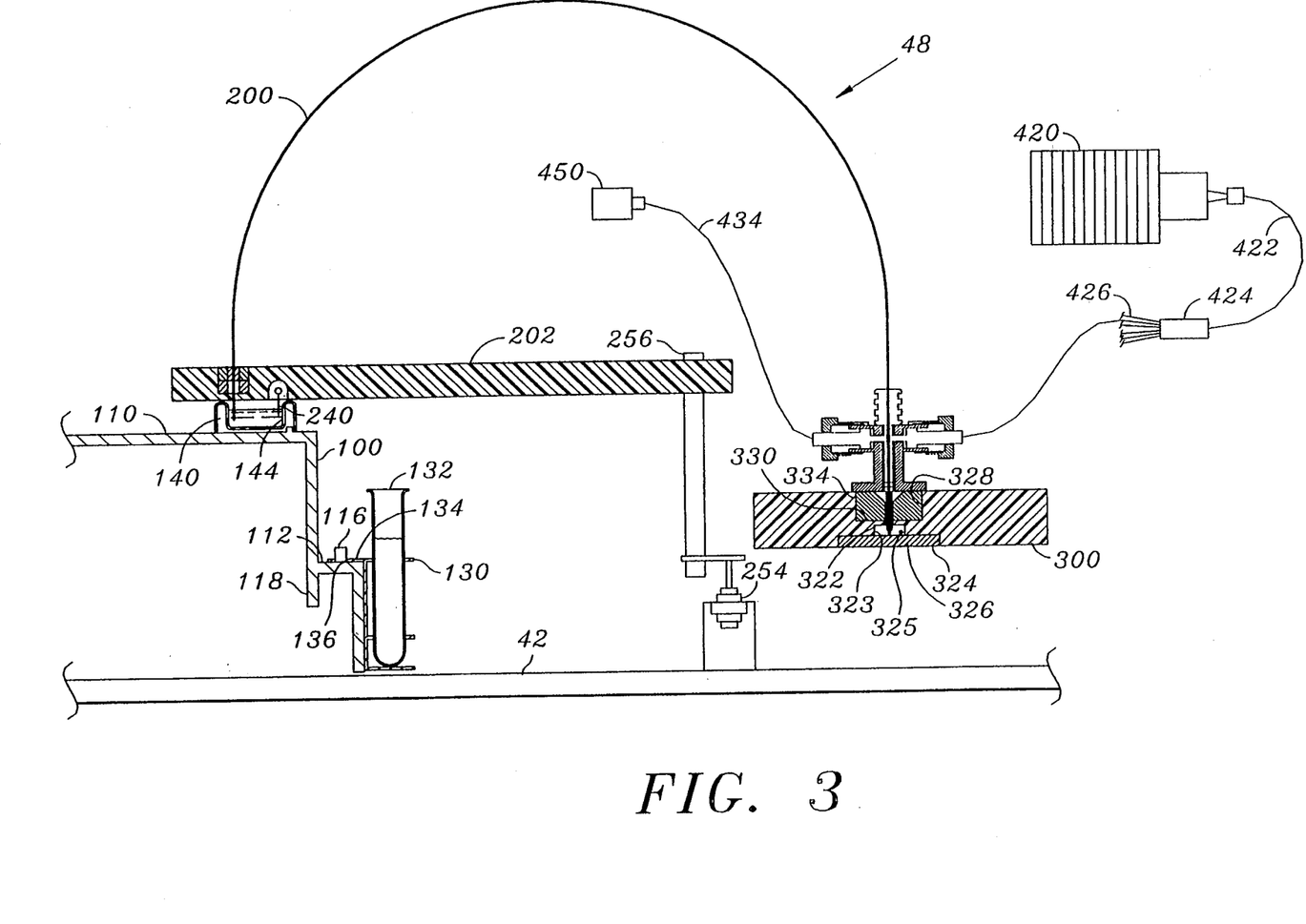
FIG. 3 is a partial section view taken along line 3—3 of FIG. 2.

Continuing the description with respect to one of the light guides 426 as seen in FIGS. 3 and 7 and it being understood that the remaining light guides 426 have corresponding structure, the input optical fiber light guide 426 terminates in a holder mechanism 428 and includes a nut configuration 430 that is removably fastened onto the arm 354. The holder mechanism 428 is positioned with respect to a window 432 formed into the flattened portion 404 of the holder 400, exposing the capillary 200. Preferably, the coating on the capillary 200 is removed to allow the passage of UV light from the end of the input optical fiber light guide 426 through the capillary to an output optical fiber light guide 434. The window and a technique for making the window are described in U.S. patent application Ser. No. 07/917,640, filed Jul. 17, 1992, entitled Capillary Electrophoresis Detection, in the names of Waska, Klein and Johnson, filed concurrently herewith, and which is incorporated herein by reference. Although the window and technique for making the window are preferrably as that described in such application, other techniques for removing the capillary coating can be used.

The output light guide 434 includes at its end a holder mechanism 436 which may be removable fixed within the arm 356 by means of a nut configuration 438. The opposite end of the output optical fiber light guide 434 is applied to a detector housing 450 that includes a suitable detector, such as a silicon photo-detector 640 (FIG. 8) to detect the light that passes through the capillary 200.

The fluid control system of the analyzer 40 includes the reservoirs 62, capillary assembly 48 (including the sample end plate 202 and the manifold plate 300), fluid control assembly 49, probe assembly 50, pipettor-dilutor assembly 52, and the waste bottle 74, as well as tubing interconnecting these elements. Such tubing described herein is not shown in FIGS. 1, 2 and 3 for the sake of simplicity but is instead shown in schematic form in FIG. 6. With reference to FIG. 6, the water bottle 64, buffer bottle 66, wash solution bottle 68, diluent bottle 70, waste bottle 74, wash station 346 and manifold 322 are connected to the fluid control assembly 49. The fluid control assembly 49 includes a buffer valve 501 and an auxiliary vent value 502 connected between the buffer bottle 66 and one end of the manifold 322 via a manifold line 503 and the tubing coupling 338. A vent tube 504 is connected between the valves 501 and 502 and has an open end. A water valve 505 is connected between the water bottle 64 and the tubing coupling 338 via the manifold line 503.

The coupling 340 in the second end of the manifold 322 is connected to a vent tube having an open end. A manifold vent valve 507 provides a valving function in the vent tube 506 near the open end of the vent tube 506. The open ends of the vent tubes 504 and 506 are above the level of the highest fluid in either the buffer bottle 66 or the water bottle 64 to avoid reagent spillage through either of the vent tubes 504, 506 if a valve failure should occur. The coupling 340 is also connected to a manifold drain valve 508 which in turn is connected to the waste bottle 74 via a mainfold drain line 509.

The vacuum for the fluid system is developed by a vacuum pump 510, part of the fluid control assembly 49. The vacuum output from the vacuum pump 510 is connected to one side of a valve 512, the other side of which is connected to a vacuum regulator 514. The regulated output of the vacuum regulator 514 is connected to the waste bottle 74 via a vacuum source line 515. A regulator bypass valve 516 is connected between the vacuum output from the vacuum pump 510 and the vacuum source line 515. The regulator 514 is provided to achieve a controlled vacuum that is used, for example, for drawing sample into the sample ends of the capillaries 200. The regulator 514 is bypassed by the valve 516 when less precise fluid control is needed, such as in simply drawing wash or buffer reagent through the capillaries 200 as is described below with respect to the operation of the analyzer 40.

A probe wash valve 517 is connected between the water bottle 64 and the inner fountain 348 of the wash station 346 and a wash vacuum valve 518 is connected between the drain port of the catch basin 349 and the manifold drain line 509. The valves 501, 502, 505, 507, 508, 512, 516, 517, and 518 are all solenoid-controlled valves and all but valve 507 are normally closed, that is, the valve is closed when the solenoid is deenergized or inactivated, and open when the solenoid is energized or activated. Valve 507 is normally opened.

Thus it is seen that the manifold line 503 is in common with the valves 502 and 505 the coupling 338. On the other hand, the manifold drain line 509 is in common with the manifold drain valve 508, wash vacuum valve 518, and the waste bottle 74.

A solenoid controlled wash solution valve 520 is connected between the NaOH wash solution bottle 68 and the tube 224 included in the group of reagent dispensing tubes 230. Similarly, a solenoid controlled normally closed buffer valve 522 is connected between the buffer bottle 66 and the tube 226 included in the group of reagent dispensing tubes 230. All of the valves described to this point, but-for the manifold vent valve 507, may be included in the fluid control assembly 49, and the valve 507 may be mounted on the upper tray 44 adjacent the open end of the vent tube 506.

The probe assembly 50 may be of a conventional design and includes a probe arm 530 which at one end is supported by a displacement mechanism 532 and at the other end supports a fluid conducting probe 534 and a needle 536. The needle 536 is used by the analyzer control circuitry (elevator controller 668 described with reference to FIG. 8) to detect the level of fluid as, for example, by sensing conductivity of the fluid into which the probe 534 and needle 536 come into contact.

The displacement mechanism 531 includes a vertical displacement motor 532 and a horizontal displacement motor 533 which together are controlled to lift and rotate the probe arm 530 and the probes 534 and 536 all in a conventional fashion.

The pipettor-dilutor assembly 52 is connected via fluid carrying tubing 560 to the fluid conducting probe 534. The conduit 560 is connected to a rotary valve 562 that connects a motor driven pipette 564 to either the diluent bottle 70 as shown in FIG. 6 or to the fluid conducting probe 534 as shown in the alternate valve position in phantom in FIG. 6. The valve 562 is controlled by a motor 566 and the pipette is controlled by means of a motor 568 connected through a screw drive mechanism 570 to the pipette 564. The pipettor-dilutor 52 is of a conventional design and may be, for example, model XL3000 available from Cavro (Sunnyvale, Calif. U.S.A.).

The analyzer 40 further includes a computer-based control system 590 to control the automated features of the analyzer 40 and to provide a suitable user interface. In the embodiment disclosed herein, and as illustrated in block form in FIG. 8, the computer control system 590 includes a central computer 592 which includes a microprocessor board 600. The microprocessor may be, for example, a type i386 available from Intel Corporation. The microprocessor board 600 is interfaced with a memory board 602 and in turn floppy and hard disk drives 604. The microprocessor board 600 is also interfaced with a keyboard 606, video board 608, serial and parallel ports 610, analog-to-digital converter 612, and an interface 614. The video board 608 in turn drives a conventional computer computer color monitor 616 having a display screen 618. It is to be understood that the computer 592 may take the form of a conventional IBM compatible personal computer (IBM is a trademark of International Business Machines Corporation) of the type very well known in the art. Further, the converter 612 and interface 614 can interface with such a computer via one or more cards that plug into the computer bus, all in a conventional fashion.

Figure 8:
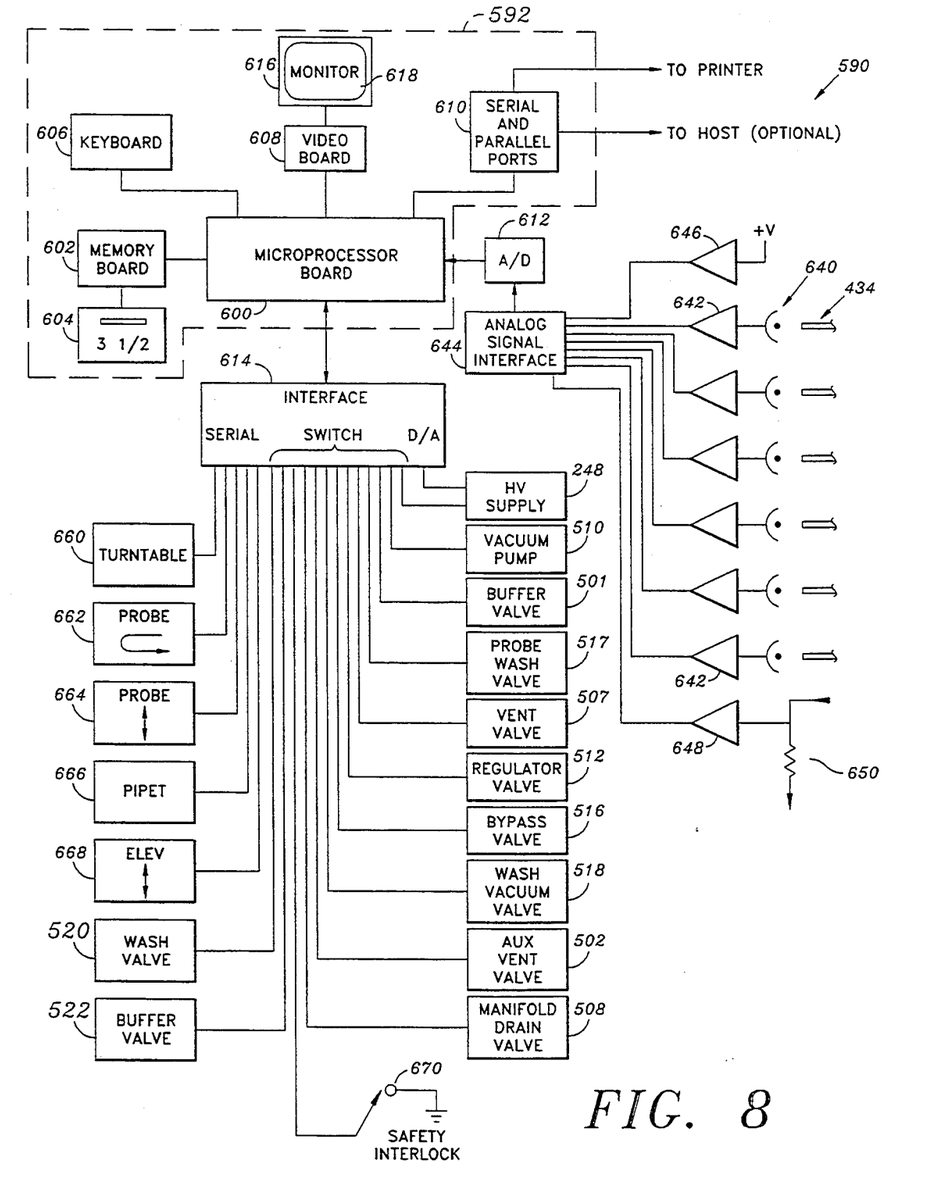
FIG. 8 is a block diagram of the control system and electronics of the analyzer of FIG. 1.

With respect to the analog portion of the control system and as described previously, output optical fiber light guides 434 are directed towards six solid state detectors 640. The output of the detectors 640 are in turn applied to six respective amplifiers 642 whose outputs are applied to an analog signal interface 644. The signal interface 644 selects the signal and scales the selected signal for analog-to-digital conversion. The selected analog output is applied to the analog-to-digital converter 612. A reference voltage amplifier 646 is also applied to the signal interface 644 for calibration of the analog signal interface 644 and the analog-to-digital converter 612.

A current monitoring resistor 650 is placed in series in the high voltage circuit formed by the high voltage power supply 248 and the capillaries 200. An amplifier 648 senses the voltage across the resistor 650 and the output of the amplifier 648 is applied to the analog signal interface 644 to thus provide a means to monitor the current through the capillaries 200.

Under the control of the microprocessor board 600, the interface 614 provides several serial data interfaces as well as switched outputs and digital-to-analog outputs for the sensing and control of assemblies and devices in the analyzer 40. Serial interfaces are provided to a turntable motor controller 660, a probe horizontal displacement motor controller 662, a probe vertical displacement motor controller 664, a pipettor-dilutor motor controller 660, and an elevator stepper motor controller 668. The motor controllers 660, 662, 664, 666 and 668, along with conventional sensing devices of the related controlled devices, control the respective motors all in a conventional fashion.

The interface 614 also includes a digital-to-analog converter that provides a voltage control signal to the high voltage power supply 248 to thereby adjust the voltage produced by the power supply 248. The interface 614 also includes switched outputs which switch on and off the high voltage power supply 248, the vacuum pump 510 and the solenoid operated valves 501, 502, 507, 508, 512, 516, 517, 518, 520 and 522. The interface 614 is responsive to a safety interlock switch 670 which is actuated when the analyzer 40 panels (not shown) are removed, thereby disabling the high voltage power supply 248 by means of the microprocessor board 600.

For the purpose of the following description of an analysis cycle of the analyzer 40, it is assumed that the analyzer 40 is in a ready state with the fluid probe 534 primed with diluent and raised to a park position above, for example, the wash station 346. Priming may be accomplished, for example, by drawing diluent into the pipettor-dilutor 52 from the diluent bottle 70, changing the position of the valve 562 to that shown by the dashed line in FIG. 6, and expelling diluent into the line 560 until the fluid probe 534 is primed. The sample end plate 202 is also raised such that the sample ends of the capillaries 200 and the electrodes 240 clear the tops of reagent segments 140 that may be carried by the turntable 100, the turntable 100 is in a home position, vacuum pump 510 and high voltage power supply 248 are off, and all valves are in the normal or deenergized state.

Before the analysis cycle begins, it is also assumed that a sample tube sector 130 is placed onto the turntable 100 at, for example, a load position 680. The sector 130 holds six sample tubes 132a through 132f, each containing a suitable sample for analysis, such as human blood serum. Also, an empty, clean reagent segment 140 is placed onto the turntable at the load position 680 inboard from the positioned sector 130 over the corresponding one of the ribs 114. For the purpose of this description, the six reservoir groups 142 in the reagent segment 140 at the load position 680 are identified as groups 142a through 142f corresponding to the six sample tubes 132a-132f, and the four reservoirs 144 in each of the groups 142a-142f are identified as reservoirs 144a through 144d.

The keyboard 606 is operated to define a capillary electrophoresis analysis cycle. Instructions Patent given by way of the keyboard 606 to the control system 590 may include, for example, the location of the sample sector 130 on the turntable 100, the number of sample tubes 132 on the sample sectors 130 (in this example, six sample tubes 132a-132a), and the analysis parameters for each batch analysis performed with respect to the sample tubes 132 carried on a sample sector 130. The analysis parameters may include whether samples are to be drawn into the capillaries 200 by vacuum or by application of high voltage, the length of time for such sample injection into the capillary 200 ends, the voltage to be applied during electrophoresis, and the length of time that electrophoresis is to be performed.

The analyzer 40 is commanded to begin the specified analysis by way of the keyboard and the control system takes over automated control of the analyzer 40. Turntable 100 is rotated to position the first sample tube 132a under the hole 222 and beneath the arc described by the fluid probe 534. The probe 534, in an initial raised park position, is rotated to a position above the first sample tube 132a. The probe assembly 50 and the pipettor-dilutor assembly 52 are controlled to lower the tip of the fluid probe 534 into the sample contained within the sample tube 132a, draw a predetermined volume of sample into the fluid probe 534, raise the probe 534 and rotate it above the first reservoir 144a of the reservoir group 142a inboard from the sample tube 132a, and lower the tip of the probe 534 into the reservoir 144a. The pipettor-dilutor assembly 52 is controlled to dispense the sample into the reservoir 144a and also dispense an additional volume of diluent into the reservoir 144a.

The probe 534 is raised, rotated and lowered into the inner fountain 348 of the wash station 346. Typically, to wash the probe, the wash valve 517, wash vacuum valve 518, and bypass valve 516 are opened, and the vacuum pump 510 is operated to flow water into the fountain 348 around the probe and remove waste liquid via the drain port in the catch basin 349. Additional diluent may be flowed from the probe 534 into the fountain 348 by operation of the pipettor-dilutor assembly 52 to assure internal cleaning of the fluid probe 534.

As an alternative, the above sample dilution cycle can be repeated but with the probe assembly 50 and the pipetor-dilutor assembly 52 controlled to draw the first dilution of the sample from the reservoir 144a into the fluid probe 534, transfer such first dilution to the fourth reservoir 144d and add a predetermined amount of diluent to the fourth reservoir 144d through the fluid probe 534. In this way, a second dilution of the sample is created for use in the electrophoretic analysis or in a second electrophoretic analysis of the sample.

The turntable 100 is rotated to position reservoirs 144b and 144c within the reservoir group 142a beneath the wash and buffer reagent tubes 224 and 226, respectively. Valves 520 and 522 are opened for a predetermined time period to dispense running buffer and wash solution into the reservoirs 144b and 144c, respectively.

The above sample, running buffer and wash solution dispensing procedures are repeated for the remaining samples in the sample tubes 132b-132f to dispense diluted sample, running buffer and wash solution into respective reservoirs 144a, 144b, and 144c, respectively, in the reservoir groups 142b through 142f.

Assuming that the capillaries 200 are not filled with running buffer, the turntable 100 is rotated so as to position the sample ends of the capillaries 200 above the reservoirs 144b in the reservoir groups 142a through 142f that contain running buffer. The elevator stepper motor 154 is controlled to lower the sample end plate 202 until it rests atop the pins 115 and the sample ends of the capillaries 200a through 200f as well as the corresponding electrodes 240 are lowered into the running buffer reservoirs 144b of the reservoir groups 142a through 142f, respectively. The vacuum pump 510 is operated and the regulator bypass valve 516 is opened to produce a vacuum through the waste bottle 74 and the manifold drain line 509. Manifold vent valve 507 is closed and manifold drain valve 508 is opened, applying vacuum to the manifold 322, thereby drawing running buffer through the capillaries 200. After a suitable predetermined time period, the vacuum pump 510 and valve 516 are deactivated. The buffer valve 501, auxiliary vent valve 502, and manifold vent valve 507 are opened and the drain valve 508 is closed to complete the filling of the manifold 322 with running buffer by gravity feed from the running buffer bottle 66. It is much more time efficient to fill the manifold 322 with running buffer by means of gravity feed rather than attempting to fill the manifold 322 with running buffer delivered through the capillaries 200 because of the extremely small inside diameter of the capillaries 200 and the corresponding very low liquid flow rates through those capillaries, even with a vacuum applied via the waste bottle 74 by means of the vacuum pump 510 and valve 516.

With the manifold 322 filled, buffer valve 501 and auxiliary vent valve 502 are closed. Because the manifold 322 is filled with buffer by gravity feed, a fluid column is supported within the vent tube 506 essentially to the level of the buffer within buffer bottle 66. This fluid column creates a hydrostatic back pressure in the manifold 322 that can slow the separating flow of samples through the capillaries and cause run-to-run variations is separation time. To prevent this, the vacuum pump 510 is operated, and bypass valve 516, manifold drain valve 508 and manifold vent valve 507 are opened to draw or sip this fluid column into the waste bottle 74 and eliminate the potential for back pressure, normalizing the fluid pressure in the manifold essentially to atmospheric or ambient pressure and thus the same pressure on the reservoirs 144.

Alternatively, the capillaries 200 may be filled prior to the commencement of the analysis cycle. This can be accomplished by positioning a reagent segment 140 onto the turntable 100, filling the reservoirs 144b in the reservoir groups 142a through 142f of the segment 140 with running buffer, and operating the elevator stepper motor 254, vacuum pump 510 and vacuum valve 516, and the buffer, vent and drain valves 501, 502, 507 and 508 in a fashion similar to that just described.

In order to load sample into the capillaries 200, the elevator stepper motor 254 is controlled to raise the sample end plate 202 such that the ends of the capillaries 200 and the electrodes 240 clear the reagent segments 140. The turntable 100 is rotated to position the sample ends of the capillaries 200 above the sample reservoirs 144a within the respective reservoir groups 142a through 142f and the elevator stepper motor 254 is controlled to lower the sample end plate 202 onto the pins 115 such that the sample ends of the capillaries 200 are within the diluted sample contained within the sample reservoirs 144a. The vacuum pump 510 and valves 512, 507 and 508 are operated to apply regulated vacuum to the manifold 322. By appropriate timing of the application of the regulated vacuum to the manifold 322, a predetermined volume of diluted samples from the six reservoirs 144a in the reservoir groups 142a-142f are drawn to the six respective sample ends of the capillaries 200a-200f.

The vacuum pump 510 and valves 512, 507 and 508 are then de-energized to release the regulated vacuum, and the sample end plate 202 is raised, turntable 100 is rotated and sample end plate 202 is again lowered to position the sample ends of the capillaries 200a-200f and the corresponding electrodes 240 into the running buffer reservoirs 144b within the respective reservoir groups 142a through 142f.

The high voltage power supply 248 is commanded to apply a high voltage across the capillaries 200. More particularly, the high voltage power supply is connected to the wire 244 which is turn connected to the six electrodes 240 that are now disposed within the buffer reservoirs 144b. The other polarity developed by the high voltage power supply 248 is connected via system ground to the manifold electrode 325 disposed within the manifold 322. By the application of this voltage, preferably in the range of approximately 6000 to 10,000 volts DC, capillary electrophoresis begins with the samples previously drawn into the sample end of capillaries 200.

With the electrophoresing voltage applied across the capillaries 200, electrophoretic separation occurs and during the electrophoresing period of, for example, two minutes to four minutes, separated samples (depending upon the mobility of the molecules in the samples) flow past the windows 432 within each of the capillaries 200. The light directed through the windows 432 between the input and output optical fiber optic light guides 426 and 434 and thus through the bores of the capillaries is periodically sampled and processed by the detectors 640, preamplifiers 642, analog signal interface 644, analog-to-digital converter 612 and the microprocessor board 600 to create digital values related to the absorbance of the sample constituents. Preferably, the values are arranged and stored for each of the capillaries 200a-200f creating six channels or arrays of data corresponding to the six capillaries 200a-200f. The values may are stored as files on one of the disk drives 604 for further manipulation and data analysis and reduction by the control system 590 or external "host" computing means.

After the sample analysis is completed and the required data is collected by the system controller, the microprocessor board 600 controls the high voltage power supply 248 to remove the electrophoresing voltage from the capillaries 200. The elevator stepper motor 254 is actuated to raise the sample end plate 202 such that the sample ends of the capillaries 200 and the electrodes 240 clear the reagent segment 140 and the turntable 100 is rotated to position the wash fluid in the reservoirs 144c beneath the sample ends of the capillaries 200. The elevator stepper motor 254 again is controlled to lower the sample end plate 202 to position the sample ends of the capillaries 200a-200f within wash solution contained in the reservoirs 144c within the reservoir groups 142a through 142f, respectively. Regulated vacuum is again applied to the manifold 322, drawing the wash solution through the capillaries 200 to the manifold 322. After a predetermined time period, the capillaries 200 are recharged with running buffer, preparing the capillaries for the next analysis. Water in the bottle 64 may be used, for example, for maintenance washing of the manifold 322 when the analyzer 40 is shut down by opening the valve 505. The capillaries 200 may be stored for a long idle period in a dry state after suitable cleaning. The vent tube 504 may be used when draining the manifold 322 via the valves 502 and 508 into the waste bottle 74 with vacuum applied.

Additional sample tube sectors 130 may be placed onto the analyzer 40 and the batch parallel analysis cycle just described may be repeated.

Thus, the analyzer 40 of the present invention enables the batch parallel analysis of samples through a plurality of capillaries, the capillaries sharing a common manifold at the detection end of the capillaries. By using the common manifold, capillary electrophoresis can be performed in a reliable, efficient manner using a analyzer that does not include complicated individual fluid channels for each of the capillaries. Capillary preparation, sample loading, electrophoresising, capillary cleaning and reloading are more efficiently accomplished by means of the common manifold, and can be more simply accomplished as, for example, by the use of gravity feed or simultaneous, parallel vacuum feed. Such simplicity eliminates additional pumps, pinch valves, rotary valves and the like.

Figure 9:
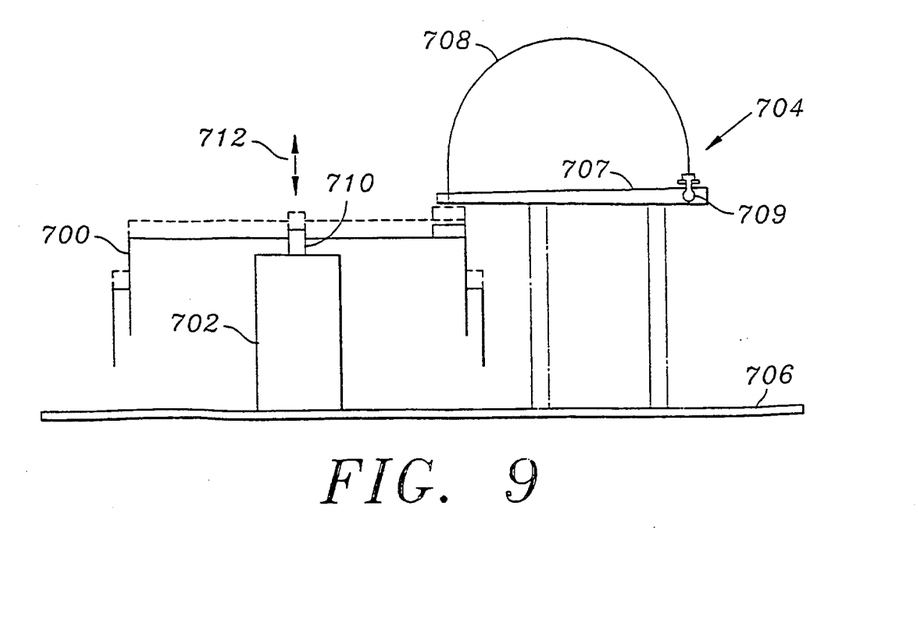
FIG. 9 is a simplified side view of another embodiment of a turntable and capillary system for use in an analyzer in accordance with the present invention.

It is to be recognized that the reagent segments 140 may be brought to the sample ends of the capillaries 200 other than by means of the elevator stepper motor 254 raising and lowering the sample end plate 202. For example, and with reference to FIG. 9, an alternative version of an analyzer in accordance with the present invention may include a turntable 700 mounted to a turntable rotational and vertical displacement mechanism 702 which is in turn supported by means of an analyzer base place 706. The mechanism includes means for raising and lowering the turntable 700, such as a vertical displacement motor and mechanism, and a rotational displacement motor and mechanism, all of conventional design. A capillary assembly 704 is fixed with respect to the base plate 706 and includes a support plate 707, a plurality of capillaries 708 and manifold 709 essentially identical to the capillaries 200 and manifold 322. Under the control of a suitable control system similar to that described above, the mechanism 702 rotates the turntable about a shaft 710 and also vertically displaces the turntable 702 upwardly and downwardly as illustrated by the arrows 712. Accordingly, the sample ends of the capillaries 708 as well as electrodes (not shown) to provide the electrical connection may be placed into and removed from reservoirs contained in reagent segments similar to those reagent segments 140 described above. With respect to either the embodiment of the analyzer 40 or the embodiment disclosed in FIG. 9, the sample ends of a plurality of capillaries are simultaneously placed within reservoirs and reagent segments, enabling batch parallel analysis and processing of samples by the capillaries.

Other modifications to the analyzer 40 are possible. For example, the capillary assembly 48 may be disposed within a temperature controlled chamber that is heated and cooled, for example, by Peltier devices to provide a thermally stable environment in which the capillaries 200 are operated. Such a temperature stabilized environment may be particularly advantageous where the batch parallel analysis performed by the capillaries must be temperature stabilized, capillary to capillary, to thereby eliminate the effects of temperature on the results detected by the analyzer 40.

It is also to be understood that the number of capillaries 200 carried in the capillary assembly 48 may be increased or decreased according, for example, to the number of samples that may be carried by sample sectors.

The control system 590 can display the electrophoretograms for the six channels on, for example, the monitor 616, in a conventional form such as an electrophoretogram with time on a horizontal axis and absorbance on the vertical axis.

The present invention is not to be limited to the embodiment disclosed herein, but is to be afforded the full scope of the appended claims and all equivalents thereof.

We claim:

1. A device for use in capillary electrophoresis comprising:
   a plurality of capillaries, each capillary having a first end and a second end;
   a plurality of wells adapted to receive corresponding first ends of the capillaries, each well receiving no more than one capillary end; and
   a conduit including means for receiving the second ends of the capillaries.

2. A device as in claim 1 wherein the conduit includes means for removably sealing the second ends of the capillaries within the conduit, thereby establishing a common liquid path between the second ends of the capillaries.

3. A device as as in claim 1 wherein the capillaries have an inside diameter in a range of about 5 to 200 microns.

4. A device as in claim 2 wherein the device further includes an electrode within the conduit.

5. A device as in claim 4 wherein the device further includes means for removably supporting the first ends of the capillaries and means for displacing the supporting means.

6. A device as in claim 4 wherein the device further includes a plurality of electrodes associated with the first ends of the capillaries in a one-to-one relationship.

7. A device as in claim 4 wherein the device further includes means for displacing the wells with respect to the first ends of the capillaries.

8. A device as in claim 4 wherein the device further includes means for displacing the first ends of the capillaries with respect to the wells.

9. A device for use with capillaries having first and second ends and a plurality of wells having predetermined spacing there between, the device including:
   first receiving means for receiving and removably holding the first ends of the capillaries in a spaced relationship corresponding to the predetermined spacing of the wells; and
   second receiving means including a conduit for removably receiving and sealing the second ends of the capillaries within the conduit to thereby establish a common liquid path between the second ends of the capillaries.

10. A device as in claim 9 wherein the first receiving means includes a plate, a plurality of openings formed through the plate, and means for removably retaining the first ends of the capillaries in the openings.

11. A device as in claim 10 wherein the device further includes an electrode disposed in the conduit.

12. A device as in claim 11 wherein the device further includes a plurality of electrodes associated with the plate openings in a one-to-one relationship.

13. A device as in claim 9 wherein the device further includes means for controllably flowing liquid into the conduit.

14. A device as in claim 13 wherein the means for flowing liquid includes a reservoir adapted to contain the liquid and valve means for controlling the flow from the reservoir to the conduit.

15. A device as in claim 14 wherein the valve means is in communication with a first end of the conduit and controllable venting means is in communication with a second end of the conduit.

16. A device as in claim 15 wherein the controllable venting means includes a vent tube having an open end above the reservoir and means for releasing liquid in the vent tube to a level substantially hydrostatically equal to the level of the conduit:

17. A device as in claim 13 wherein the device further includes means for relieving hydrostatic pressure on the conduit.

18. A device as in claim 10 wherein the second receiving means is supported by the plate.

19. An apparatus for positioning capillaries in a capillary electrophoresis system with respect to reagent segments wherein the reagent segments have a plurality of wells and wherein each capillary has a first end and a second end, the apparatus comprising:
   means for simultaneously positioning the first end of each of the capillaries into selected distinct ones of the reagent segment wells; and
   a manifold defining a common conduit including means adapted for receiving the second end of each of the capillaries into the common conduit and thereby establishing a common liquid path between the second ends of the capillaries.

20. An apparatus for positioning capillaries in a capillary electrophoresis system with respect to reagent segments wherein the reagent segments have a plurality of wells, comprising:
   a plurality of capillaries, each capillary having a first end and a second end;
   means for simultaneously positioning a first end of each of the capillaries into selected distinct ones of the reagent segment wells;
   a manifold defining a common conduit including means for receiving the second end of each of the capillaries into the common conduit and thereby establishing a common liquid path between the second ends of the capillaries; and
   an electrode in the manifold.

21. An automated capillary electrophoresis system for the analysis of samples contained in sample vessels and reagent segments wherein the reagent segments have a plurality of wells, comprising:
   a plurality of capillaries, each capillary having a first end and a second end;
   means for simultaneously positioning a first end of each of the capillaries into selected ones of the reagent segment wells;
   a manifold for receiving the second end of each of the capillaries, the manifold including sealing means for removably sealing the second end of the capillaries into fluid communication with the manifold;
   an electrode in the manifold;
   means for supplying a buffer solution to the manifold;
   detection means for simultaneously detecting a selected physical property of the liquids within the capillaries; and
   electrode means for positioning an electrode into the selected ones of the reagent segment wells into which the first ends of the capillaries are positioned.

22. An automated capillary electrophoresis system used for the analysis of samples contained in sample vessels and reagent segments wherein the reagent segments have a plurality of wells, comprising:
   a turntable;
   means on the turntable for receiving and removably retaining a plurality of the sample vessels;
   means on the turntable for receiving and removably retaining a plurality of the reagent segments;
   means for rotating the turntable to selectively position the reagent segment wells;
   a plurality of capillaries, each capillary having a first and a second end;
   means for simultaneously positioning a first end of each of the capillaries into selected ones of the reagent segment wells;
   a manifold for receiving a second end of each of the capillaries, the manifold including sealing means for removably sealing the second end of the capillaries into fluid communication with the manifold;
   detection means for simultaneously detecting a selected physical property of the liquids within the capillaries;
   first electrode means for connecting a first potential to the first end of the capillaries; and
   second electrode means for connecting a second potential to the second end of the capillaries.

23. A system as in claim 22 wherein the means for positioning includes turntable elevator means for displacing the turntable vertically with respect to the first ends of the capillaries.

24. A system as in claim 23 wherein the turntable elevator means further includes means for rotating the turntable to thereby position selected portions of the turntable under the first ends of the capillaries.

25. A system as in claim 22 wherein the means for positioning includes a capillary first end elevator means for displacing the first ends of the capillaries with respect to the turntable.

26. A system as in claim 22 wherein the positioning means includes a plate, a plurality of openings formed through the plate, and means for removably retaining the first ends of the capillaries in the openings.

27. A system as in claim 26 wherein the retaining means includes first magnets fixed within the openings and second magnets fixed on the capillaries proximate the ends of the capillaries, and the first and second magnets are arranged to provide attractive magnetic force when the capillaries are removably retained within the openings.

28. A system as in claim 26 wherein the plate includes reagent delivery tubes adapted to deliver reagents to selected ones of the reagent segment wells.

29. A system as in claim 22 wherein the system further includes sample probe means for dispensing a sample from a sample vessel retained on the turntable into one or more reagent segment wells.

30. A device as in claim 22 wherein the device further includes sample dilution means for diluting a sample contained in one reagent segment well into another reagent segment well.

31. A system as in claim 22 wherein the system further includes means for simultaneously drawing fluid through the capillaries.

32. A system as in claim 31 wherein the means for drawing includes a vacuum generating means for controllably connecting a vacuum to the manifold.

33. A system as in claim 32 wherein the system further includes a waste reservoir in fluid communication between the vacuum generating means and the manifold and the vacuum generating means further includes means for generating a first vacuum and a second vacuum greater than the first.

34. A system as in claim 32 wherein the system further includes means for controllably flowing liquid into the manifold.

35. A system as in claim 34 wherein the means for flowing liquid includes a reservoir adapted to contain the liquid and valve means for controlling flow from the reservoir to the manifold.

36. A system as in claim 35 wherein the manifold includes a first end and a second end and the means for removably sealing the second ends of the capillaries is disposed between the first and second ends of the manifold.

37. A system as in claim 36 wherein the valve means is connected to the first end of the manifold and controllable venting means is connected to the second end of the manifold.

38. A system as in claim 37 wherein the controllably venting means includes a vent tube having an open end above the level of the reservoir and means for releasing liquid in the vent tube to substantially the level of the manifold.

39. A system as in claim 37 wherein the system includes means for controlling hydrostatic pressure upon liquid within the manifold to substantially ambient pressure.

40. A system as in claim 22 wherein the detection means includes a light source, a plurality of input fiber optic light guides directing light from the light source to an optical interface at corresponding ones of capillaries, a plurality of output fiber optic light guides receiving light from each optical interface, and a plurality of light detectors receiving light from the output fiber optic light guides.

41. A system as in claim 40 wherein the optical interface includes means for removably receiving the capillaries.

42. A system as in claim 41 wherein the removably receiving means includes a holder formed around each capillary, the holder having a flattened portion and a window formed into the flattened portion, the window exposing the capillary carried within the holder, and support structures adapted to receive the holders, the support structures fixed to position a holder within the sealing means.

43. A capillary assembly comprising a length of capillary tubing having an inside diameter in the range of about 25 microns to 75 about microns, the length of tubing having first and second open ends, a magnet fixed proximate the first end of the tubing, and a holder fixed proximate the second end of the tubing, the holder having a flattened portion and a window formed into the flattened portion, the window exposing the capillary carried within the holder.

44. A method of performing capillary electrophoresis, comprising the steps of:
 filling a plurality of capillaries with a liquid;
 drawing a plurality of samples to be analyzed into first ends of corresponding ones of the capillaries;
 placing the first ends into a liquid;
 removably sealing second ends of the capillaries into a manifold and filling the manifold with a liquid; and
 applying an electrophoresising voltage to the capillaries.

45. A method as in claim 44 wherein the liquid is a buffer.

46. A method as in claim 45 wherein the step of placing the first ends into a liquid includes placing the first ends into a plurality of separate reservoirs containing the buffer.

47. A device for use with a plurality of capillaries and a plurality of wells, the capillaries having first and second ends, the device including a plate having a manifold formed therein, the plate further including sealing means for removably sealing the second ends of the capillaries within the manifold, the device further including receiving means carded by the plate for receiving and removably holding the first ends of the capillaries in a spaced relationship such that each capillary first end is adapted to be received by a single well.

48. A device for use with a plurality of capillaries and a plurality of wells, the capillaries having first and second ends and the wells having predetermined spacing therebetween, the device including a plate having a manifold formed therein, the plate further including sealing means for removably sealing the second ends of the capillaries within the manifold, the device further including receiving means carried by the plate for receiving and removably holding the first ends of the capillaries in a spaced relationship corresponding to the predetermined spacing of the wells.

49. A device as in claim 48 wherein the device further includes an electrode disposed within the conduit.

50. A device as in claim 49 wherein the device further includes means for supporting the wells and means for displacing the wells so as to bring the wells into operative position with respect to the receiving means.

51. A device for use with a plurality of capillaries and a plurality of wells, the capillaries having first and second ends and the wells having predetermined spacing therebetween, the device including:
 a plate having a manifold formed therein and sealing means for removably sealing the second ends of the capillaries within the manifold;
 receiving means carried by the plate for receiving and removably holding the first ends of the capillaries in a spaced relationship corresponding to the predetermined spacing of the wells; and
 means for supporting the wells and for displacing the wells so as to bring the wells into operative position with respect to the receiving means.

52. A device for use with a plurality of capillaries and a plurality of wells, the capillaries having first and second ends and the wells having predetermined spacing therebetween, the device including:
 a plate having a manifold formed therein, the plate further including a plurality of openings formed in the plate and in communication with the manifold and sealing means for removably sealing the second ends of the capillaries within the manifold;
 receiving means carded by the plate for receiving and removably holding the first ends of the capillaries in a spaced relationship corresponding to the predetermined spacing of the wells such that a well receives no more than one capillary first end;
 means for supporting the wells and for displacing the wells so as to bring the wells into operative position with respect to the receiving means;
 a reservoir; and
 a valve in fluid communication between the reservoir and the conduit and adapted for controllably flowing a fluid contained in the reservoir into the manifold.

53. A device as in claim 52 wherein the device further includes means for generating a vacuum and for controllably connecting the vacuum to the manifold.

54. A method of performing capillary electrophoresis, comprising the steps of:
   filling a plurality of capillaries with a liquid;
   drawing a plurality of samples to be analyzed from discrete reservoirs into first ends of corresponding ones of the capillaries;
   placing the first ends into discrete reservoirs containing a liquid;
   removably sealing second ends of the capillaries into a manifold and filling the manifold with a liquid; and
   applying an electrophoresising voltage to the capillaries.

55. A method as in claim 54 wherein the liquid is a buffer.

56. A capillary assembly comprising a length of capillary tubing having an inside diameter in the range of about five microns to two hundred microns, the length of tubing having first and second open ends, a magnet fixed proximate the first end of the tubing, and a holder fixed proximate the second end of the tubing, the holder having a flattened portion and a window formed into the flattened portion, the window exposing the capillary carried within the holder.

* * * * *